United States Patent
Na et al.

(10) Patent No.: US 11,913,020 B2
(45) Date of Patent: Feb. 27, 2024

(54) METHOD FOR IMPROVING STEM CELL MIGRATION USING ETHIONAMIDE

(71) Applicant: Samsung Life Public Welfare Foundation, Seoul (KR)

(72) Inventors: Duk Lyul Na, Seoul (KR); Jong Wook Chang, Seoul (KR); Hyo Jin Son, Seoul (KR)

(73) Assignee: SAMSUNG LIFE PUBLIC WELFARE FOUNDATION, Seoul (KR)

( * ) Notice: Subject to any disclaimer, the term of this patent is extended or adjusted under 35 U.S.C. 154(b) by 486 days.

(21) Appl. No.: 16/760,004

(22) PCT Filed: Oct. 8, 2018

(86) PCT No.: PCT/KR2018/011811
§ 371 (c)(1),
(2) Date: Apr. 28, 2020

(87) PCT Pub. No.: WO2019/088480
PCT Pub. Date: May 9, 2019

(65) Prior Publication Data
US 2020/0339948 A1    Oct. 29, 2020

(30) Foreign Application Priority Data
Oct. 30, 2017   (KR) .................. 10-2017-0142231

(51) Int. Cl.
*C12N 5/0735*   (2010.01)
*A61K 35/51*    (2015.01)
*C12N 5/0775*   (2010.01)

(52) U.S. Cl.
CPC ............ *C12N 5/0606* (2013.01); *A61K 35/51* (2013.01); *C12N 5/0663* (2013.01); *C12N 5/0665* (2013.01); *C12N 5/0668* (2013.01); *C12N 2501/999* (2013.01)

(58) Field of Classification Search
CPC ... C12N 5/0606; C12N 5/0665; C12N 5/0662
See application file for complete search history.

(56) References Cited

U.S. PATENT DOCUMENTS

2015/0118748 A1*   4/2015   Ra .................. C12N 5/0667
                                                            435/325

FOREIGN PATENT DOCUMENTS

| KR | 1020130085863 | | 7/2013 | |
|---|---|---|---|---|
| KR | 1020150004762 | | 6/2016 | |
| WO | 2015009884 A1 | | 1/2015 | |
| WO | WO-2015009884 A1 | * | 1/2015 | ........... C12N 5/0606 |

OTHER PUBLICATIONS

Somoza et al. Neuropotency of Human Mesenchymal Stem Cell Cultures: Clonal Studies Reveal the Contribution of Stem Cell Plasticity and Cell Contamination. Biology of Blood and Bone Marrow Transplantation 2008; 14:546-555 (Year: 2008).*
Gibco MEM product information sheet, 2019-2022 (Year: 2019).*
Fruscione et al. Regulation of human mesenchymal stem cell functions by an autocrine loop involving NAD+ release and P2Y11-mediated signaling. Stem Cells and Development 2011, 20;7:1183-1198. (Year: 2011).*
Canto et al. AMPK regulates energy expenditure by modulating NAD+ metabolism and SIRT1 activity. Nature 2009, 458:1056-1062. (Year: 2009).*
Botti et al. SIRT1 inhibition affects angiogenic properties of human MSCs. Biomed Research International 2014, 2014;1-12. (Year: 2014).*
Kawai et al. Acetylation-deacetylation of the transcription factor Nrf2 (Nuclear factor erythroid 2-related factor 2) regulates its transcriptional activity and nucleocytoplasmic localization. Gene Regulation 2011, 286;9:7629-7640. (Year: 2011).*
Bogan et al. Nicotinic acid, nicotinamide, and nicotinamide riboside: a molecular evaluation of NAD+ precursor vitamins in human nutrition. Annual Reviews of Nutrition 2008, 28:115-130. (Year: 2008).*
Guo et al. Cold exposure induces intestinal barrier damage and endoplasmic reticulum stress in the colon via the SIRT1/Nrf2 signaling pathway. Frontiers in Physiology 2022, 13:1-12. (Year: 2022).*
Zhang et al. SIRT1 inactivation switches reactive astrocytes to an antiinflammatory phenotype in CNS autoimmunity. Journal of Clinical Investigation 2022, 132;22:e151803. (Year: 2022).*
Li Y, et al. Biochem Biophys Res Commun. May 11, 2007; 356(3): 780:4, Epub Mar. 19, 2007, Insulin-Like Growth Factor 1 Enhances The Migratory Capacity of Mesenchymal Stem Cell.s, 1 page.
Pittenger, et al., Science, Multilineage Potential of Adult Human Mesenchymal Stem Cells, vol. 284,, dated Apr. 2, 1999, www.sciencemag.org, 6 pages.
Van et al, Cytological and Enzymological Characterization of Adult Human Adipocyte Precursors in Culture, The Journal of Clinical Investigation, vol. 58, Sep. 1976; pp. 699-704.
Miller et al., CXCR4 Signaling in the Regulation of Stem Cell Migration and Development, J. Neuroimmunol., 2008, Jul. 31, 198( ); 31-38.
Katrahalli et al, The Effect of Anti-Tubercular Drug, Ethionamide on the Secondary Structure of Serum Albumins: A Biophysical Study, Journal of Pharmaceutical and Biomedical Analysis, 59 (2012), 102-108.

*Primary Examiner* — Allison M Fox
*Assistant Examiner* — Jennifer S Spence
(74) *Attorney, Agent, or Firm* — Harness, Dickey & Pierce, P.L.C.

(57) ABSTRACT

The present invention relates to a medium composition for improving stem cell migration, which includes ethionamide, and a use thereof. According to the present invention, the migration of stem cells may be effectively improved by the adjustment of a culture environment, which is a simple and safe method, without using gene manipulation or a viral vector, and the stem cells improved in migration by the method may be effectively used as a stem cell therapeutic agent that is able to function by rapidly migrating to the damaged region after transplantation.

5 Claims, 5 Drawing Sheets

(56) References Cited

OTHER PUBLICATIONS

Extended European Search Report from corresponding European Patent Application No. 18872429.8, dated Jul. 7, 2021.
Na-Hee Lee et al., "Ethionamide Preconditioning Enhances the Prolileration and Migration 01 Human Wharton's Jelly-Derived Mesenchymal Stem Cells" International Journal of Molecular Sciences, vol. 21, No. 19, Sep. 23, 2020 (Sep. 23, 2020), p. 7013, XP055818853.

* cited by examiner

METHOD FOR IMPROVING STEM CELL MIGRATION USING ETHIONAMIDE

RELATED APPLICATIONS

This application is a 35 U.S.C. § 371 filing of International Patent Application No. PCT/KR2018/011811, filed Oct. 8, 2018, which claims the benefit of Korean Application No. 10-2017-0142231, filed Oct. 30, 2017, each of which is incorporated herein by reference in its entirety.

TECHNICAL FIELD

The present invention relates to a medium composition for improving stem cell migration, which includes ethionamide, and a use thereof.

BACKGROUND ART

Stem cells are cells having a self-replication ability and an ability to differentiate into two or more cells. Such stem cells may be classified into totipotent stem cells, pluripotent stem cells and multipotent stem cells according to a differentiation ability, and the multipotent stem cells refer to stem cells capable of differentiating into cells specific for tissue and an organ having the cells.

Mesenchymal stem cells are known as cells involved in the regeneration, treatment and immune response of tissue as well as multipotency, and efforts have been made to develop mesenchymal stem cells isolated from umbilical cord blood, bone marrow, etc., and cultured as a therapeutic agent for various diseases using the above-described properties. Particularly, in the development of a stem cell therapeutic agent using mesenchymal stem cells, since stem cell migration ability is an important property to allow the stem cells to act in a lesion within a short time or to improve engraftment ability after cell transplantation, stem cell migration and an induction mechanism are recognized as significant tasks.

Thus, while research has been conducted to promote the proliferation and migration ability of stem cells, and as an example, it has been reported that insulin-like growth factor-1 (IGF-1) promotes the proliferation and migration of some stem cells (Biochem Biophys Res Commun. 2007 May 11; 356(3):780-4.), the mechanisms of cell migration and induction after transplantation of mesenchymal stem cells are not yet known. When the migration ability of the mesenchymal stem cells is lost or reduced, a therapeutic effect is significantly reduced, and thus a method of effectively improving the migration and enhancing the effect of a stem cell therapeutic agent is needed.

DISCLOSURE

Technical Problem

Therefore, the inventors had intensively studied a method of improving the migration of stem cells, and thereby found that ethionamide known as a conventional antibiotic can effectively improve the migration of stem cells, and thus the present invention was completed.

Accordingly, the present invention is directed to providing a medium composition for improving stem cell migration, which includes ethionamide, and a use thereof.

However, technical problems to be solved in the present invention are not limited to the above-described problems, and other problems which are not described herein will be fully understood by those of ordinary skill in the art from the following descriptions.

Technical Solution

The present invention provides a medium composition for improving stem cell migration, which includes ethionamide.

In one embodiment of the present invention, the ethionamide is included in a medium at a concentration of 1 to 500 µM.

In another embodiment of the present invention, the medium is Minimum Essential Medium (α-MEM) supplemented with fetus bovine serum (FBS) and gentamicin.

In still another embodiment of the present invention, the stem cells are embryonic stem cells or adult stem cells.

In yet another embodiment of the present invention, the adult stem cells may be mesenchymal stem cells derived from one or more types of tissue selected from the group consisting of the umbilical cord, umbilical cord blood, bone marrow, fat, muscle, nerve, skin, amniotic membrane and placenta.

In yet another embodiment of the present invention, the medium increases the expression of a chemokine (C-X-C motif) receptor 4 (CXCR4) gene in a stem cell.

In addition, the present invention provides a method of improving stem cell migration, which includes culturing stem cells in the medium composition.

In addition, the present invention provides stem cells improved in migration, which is obtained by the above-described method.

In one embodiment of the present invention, the stem cells are mesenchymal stem cells derived from one or more types of tissue selected from the group consisting of the umbilical cord, umbilical cord blood, bone marrow, fat, muscle, nerve, skin, amniotic membrane and placenta.

Advantageous Effects

The inventors experimentally confirmed that, as a result of ethionamide treatment on human mesenchymal stem cells, the migration of the stem cells is significantly improved. Therefore, according to the present invention, the migration of stem cells can be effectively improved by the adjustment of a culture environment, which is a simple and safe method, without using gene manipulation or a viral vector, and the stem cells improved in migration by the method can be effectively used as a stem cell therapeutic agent that can function by rapidly migrating to the damaged region after transplantation.

MODES OF THE INVENTION

The present invention provides a medium composition for improving stem cell migration, which includes ethionamide.

Conventionally, ethionamide (2-ethylpyridine-4-carbothioamide) having the following chemical structure is a thionamide-based antibiotic known for its treatment of an infectious disease caused by bacteria, but in the present invention, the use of ethionamide to improve stem cell migration was first found.

[Ethionamide]

The inventors confirmed an effect of improving stem cell migration by ethionamide treatment according to an exemplary embodiment.

In one embodiment of the present invention, it was observed through a wound healing assay that human umbilical cord mesenchymal stem cells cultured after ethionamide treatment are significantly improved in cell migration, compared to the same type of stem cells which are not treated with ethionamide, and confirmed that the migration ability is highly shown in proportion to a concentration of treated ethionamide (refer to Example 2).

In another embodiment of the present invention, according to a Transwell assay using human umbilical cord mesenchymal stem cells cultured with ethionamide treatment and the same type of mesenchymal stem cells cultured without ethionamide treatment, it was confirmed that, when ethionamide is treated, the invasion of mesenchymal stem cells increases in proportion to a concentration of the treated ethionamide (refer to Example 3).

In still another embodiment of the present invention, it was confirmed through real-time PCR that an expression level of CXCR4, which is a migration-related gene, was significantly increased in human umbilical cord mesenchymal stem cells by ethionamide treatment (refer to Example 4).

Such results show that the migration of human mesenchymal stem cells can be effectively improved by ethionamide treatment.

There is no limitation on a concentration of ethionamide included in the medium, but the ethionamide is preferably included at 1 to 500 µM, more preferably 10 to 200 µM, and still more preferably 100 µM.

In the present invention, there is no limitation on the medium used in cell culture, but for example, the medium is preferably α-MEM supplemented with FBS and gentamicin, and more preferably, the FBS may be contained at 10%, and the gentamicin may be contained at 50 µg/mL.

The term "stem cells" used herein refers to undifferentiated cells, which are cells having a self-replication ability and an ability to differentiate into two or more different types of cells. The stem cells of the present invention may be autologous or allogeneic stem cells, and may be derived from any type of animal such as a human or non-human mammal. The stem cells may be derived from an adult or embryo, but the present invention is not limited thereto.

In the present invention, the adult stem cells derived from an adult may be mesenchymal stem cells, human tissue-derived mesenchymal stromal cells, human tissue-derived mesenchymal stem cells, multipotent stem cells or amniotic epithelial cells, and preferably, mesenchymal stem cells, but the present invention is not limited thereto. The mesenchymal stem cells may be mesenchymal stem cells derived from the umbilical cord, umbilical cord blood, bone marrow, fat, muscle, nerve, skin, amniotic membrane and placenta, but the present invention is not limited thereto.

In the present invention, the "Wharton's jelly derived stem cells" include all of stem cells isolated from the umbilical cord, and the umbilical cord refers to a cord-like structure connecting the mother body and a fetus at the navel such that the mammalian fetus can grow at the placenta, and may, generally, refer to tissue consisting of three blood vessels, that is, two navel arteries and one navel vein, surrounded by Wharton's jelly.

In the present invention, the "placenta-derived stem cells" include all of stem cells isolated from the placenta, and preferably include 4 types of stem cells isolated from the human placenta isolated from the body, that is, (1) human amniotic epithelial cells (hAECs), (2) human amniotic mesenchymal stromal cells or human amniotic mesenchymal stem cells (hAMSCs), (3) human chorionic mesenchymal stromal cells or human chorionic mesenchymal stem cells (hCMSCs), and (4) human chorionic trophoblastic cells (hCTCs).

The isolation of mesenchymal stem cells may be performed by a method well known to those of ordinary skill in the art, for example, the methods disclosed in the literature written by Pittenger et al. (Science 284: 143, 1999) and Van et al. (J. Clin. Invest., 58: 699, 1976).

In the present invention, the improvement in stem cell migration may refer to the improvement in stem cell migration ability, and an increase in the expression of chemokine (C-X-C motif) receptor 4 (CXCR4), which is a gene related to stem cell migration, and ultimately includes an improvement in migration activity from a transplanted region to a treatment region in cell transplantation.

In addition, the present invention provides a method of improving stem cell proliferation, which includes culturing stem cells in the medium composition, and stem cells improved in migration, which are obtained thereby.

In addition, the present invention provides a cell therapeutic agent for treating various diseases, which includes the stem cells.

Hereinafter, to help in understanding the present invention, exemplary examples will be suggested. However, the following examples are merely provided to more easily understand the present invention, and not to limit the present invention.

EXAMPLES

Example 1

Preparation of Human Umbilical Cord Mesenchymal Stem Cells

Human umbilical cord mesenchymal stem cells were isolated by the following method, after umbilical cords were obtained according to the standards approved by IRB (IRB #2015-09-023-003) of Samsung Seoul Hospital.

First, the umbilical cord tissue was cut to 3 to 4 cm and treated with a collagenase solution (Gibco, USA) for 60 to 90 minutes and then treated with 0.25% trypsin (Gibco, USA) for 30 minutes at 37° C. to degrade the extracellular matrix. Afterward, cells were obtained by adding FBS (Biowest, USA) and performing centrifugation at 1000×g for 10 minutes, and incubated in MEM (Gibco, USA) supplemented with 10% FBS and 50 μg/mL gentamicin (Gibco, USA) at 37° C. in a 5% $CO_2$ environment, and then the mesenchymal stem cells at passage 5 or 6 were used for the experiment.

Example 2

Confirmation of Improvement in Migration of Human Mesenchymal Stem Cells by Ethionamide Treatment To examine the effect of improving the migration of human mesenchymal stem cells by ethionamide treatment, a wound healing assay was performed. To this end, human umbilical cord mesenchymal stem cells ($5\times10^4$ cells) prepared according to the method described in Example 1 were dispensed into a 6-well plate, and simultaneously treated with ethionamide at 10 or 100 μM, followed by incubation for 24 hours. Subsequently, to inhibit cell proliferation, the cells were treated with mitomycin C at 10 μg/mL to allow a reaction for 2 hours, a scratch was made on the plate using a tip, followed by exchanging the medium with a fresh medium.

Figure 1A:
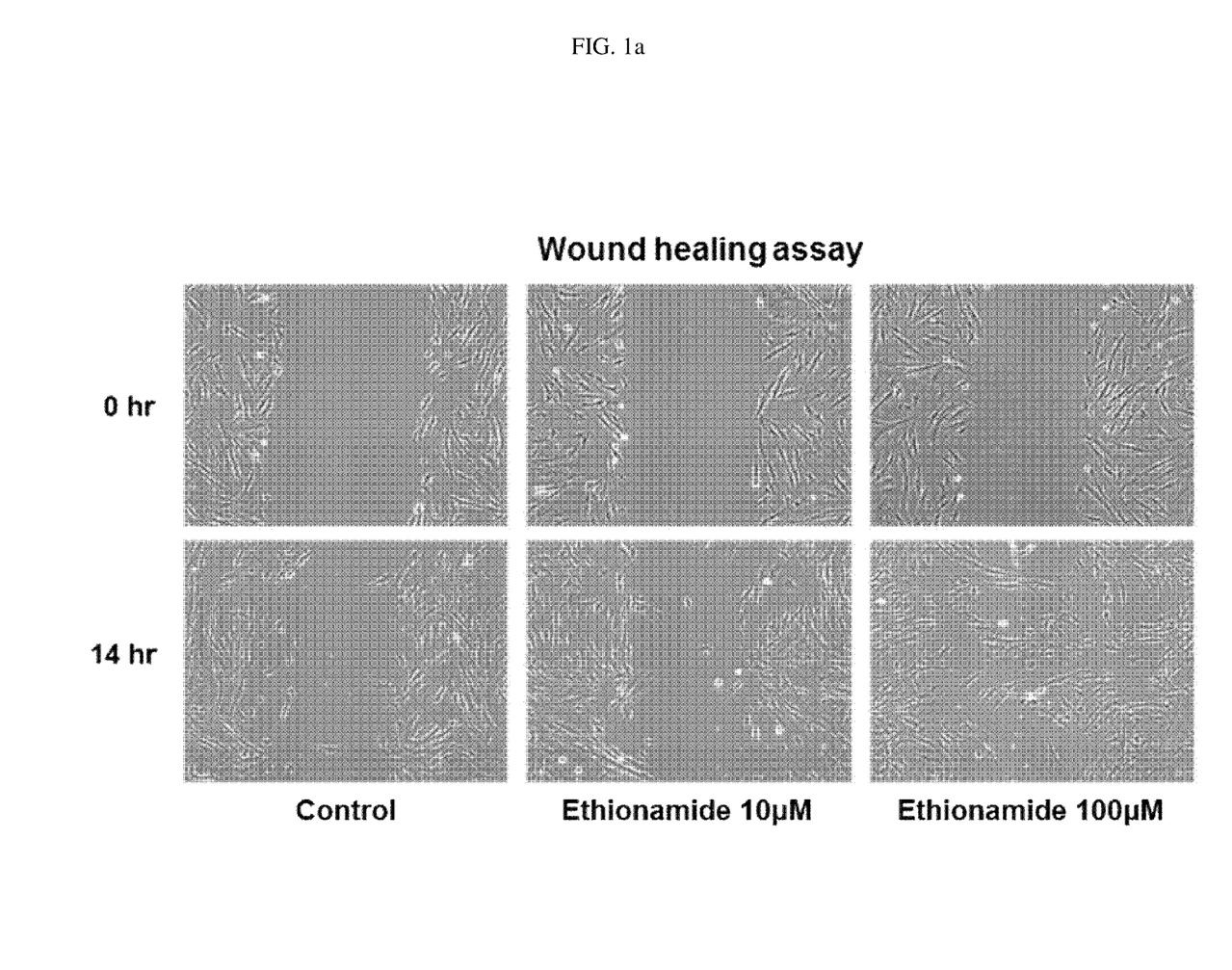
FIG. 1A is a set of microscopic images after a wound healing assay to verify an improved migration ability of human mesenchymal stem cells by ethionamide treatment.
Figure 1B:
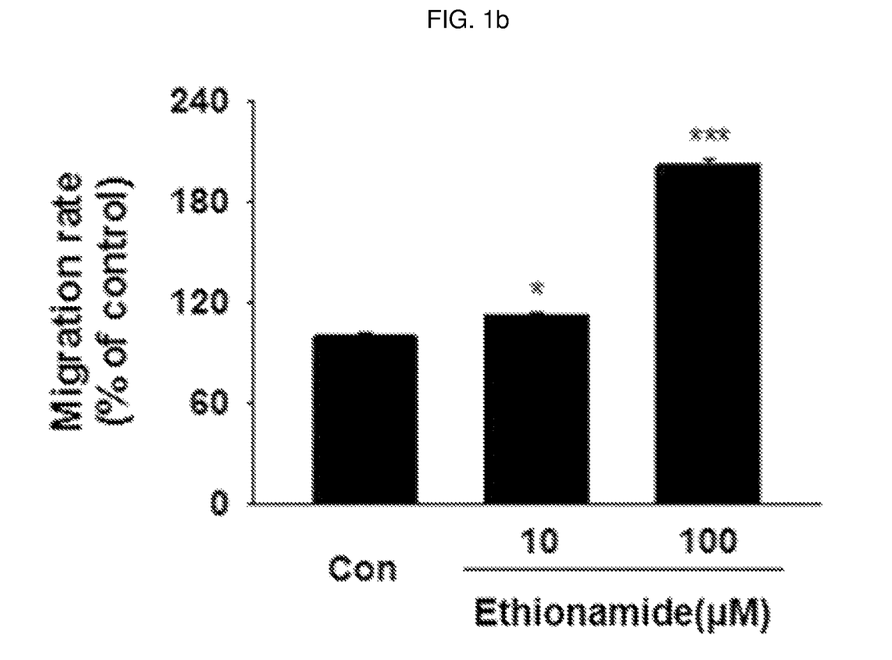
FIG. 1B is a quantitative result of measuring the number of migrating cells after a wound healing assay.

As a result of observation of the scratch after 14 hours, as shown in FIG. 1A, compared to a control not treated with ethionamide, in the ethionamide-treated groups (10 μM of ethionamide and 100 μM of ethionamide), stem cell migration was observed, and such a cell migration ability was proportional to a concentration of the treated ethionamide. To quantitatively assess the result, the number of migrating stem cells was counted, and as shown in FIG. 1B, it was confirmed that the migration ability of human mesenchymal stem cells is significantly increased by ethionamide treatment.

Example 3

Confirmation of Improvement in Invasion of Human Mesenchymal Stem Cells by Ethionamide Treatment In addition to the result of Example 2, to examine the effect of improving the invasion of human mesenchymal stem cells by ethionamide treatment, a Transwell assay was performed. To this end, the human umbilical cord mesenchymal stem cells ($5\times10^4$ cells) prepared by the method described in Example 1 were dispensed into a Transwell plate (Costar, USA) with an 8.0 μm pore size, and treated with ethionamide at 10 or 100 μM, followed by incubation for 24 hours. Subsequently, the cells were fixed with 4% paraformaldehyde and stained with hematoxylin, the inner side of the Transwell was wiped with a cotton tip, and then the number of cells present on the bottom surface of the Transwell was measured using a microscope.

Figure 2A:
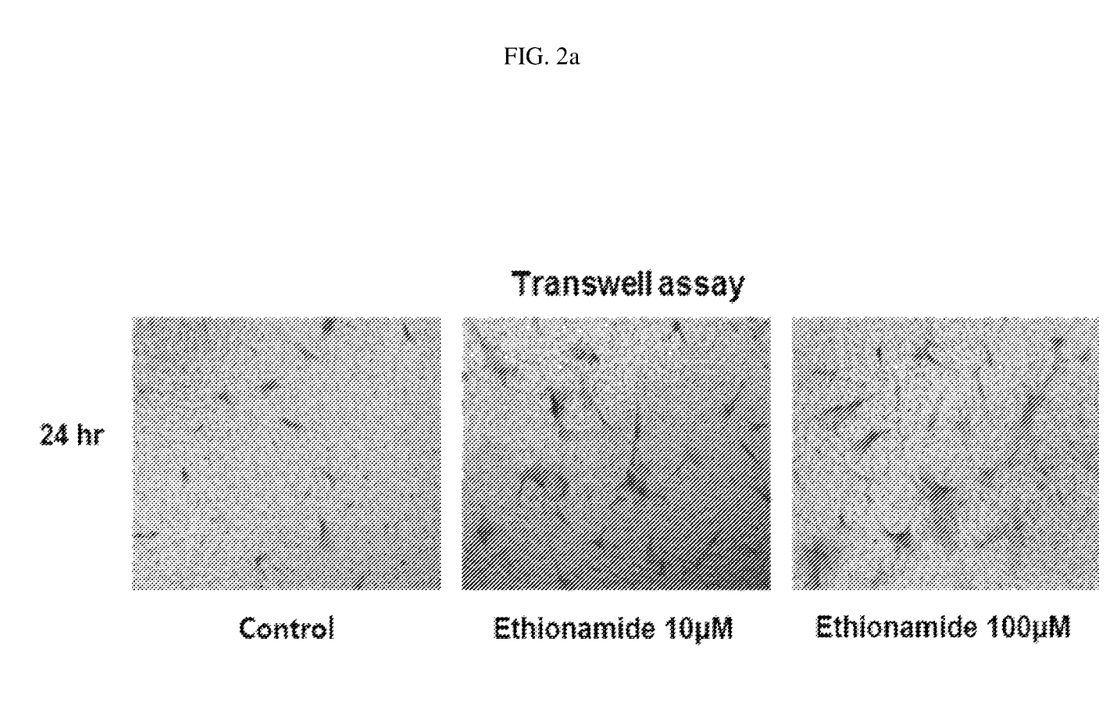
FIG. 2A shows hematoxylin-stained cells observed using a microscope after a Transwell assay is performed to verify improved invasion of human mesenchymal stem cells by ethionamide treatment.
Figure 2B:
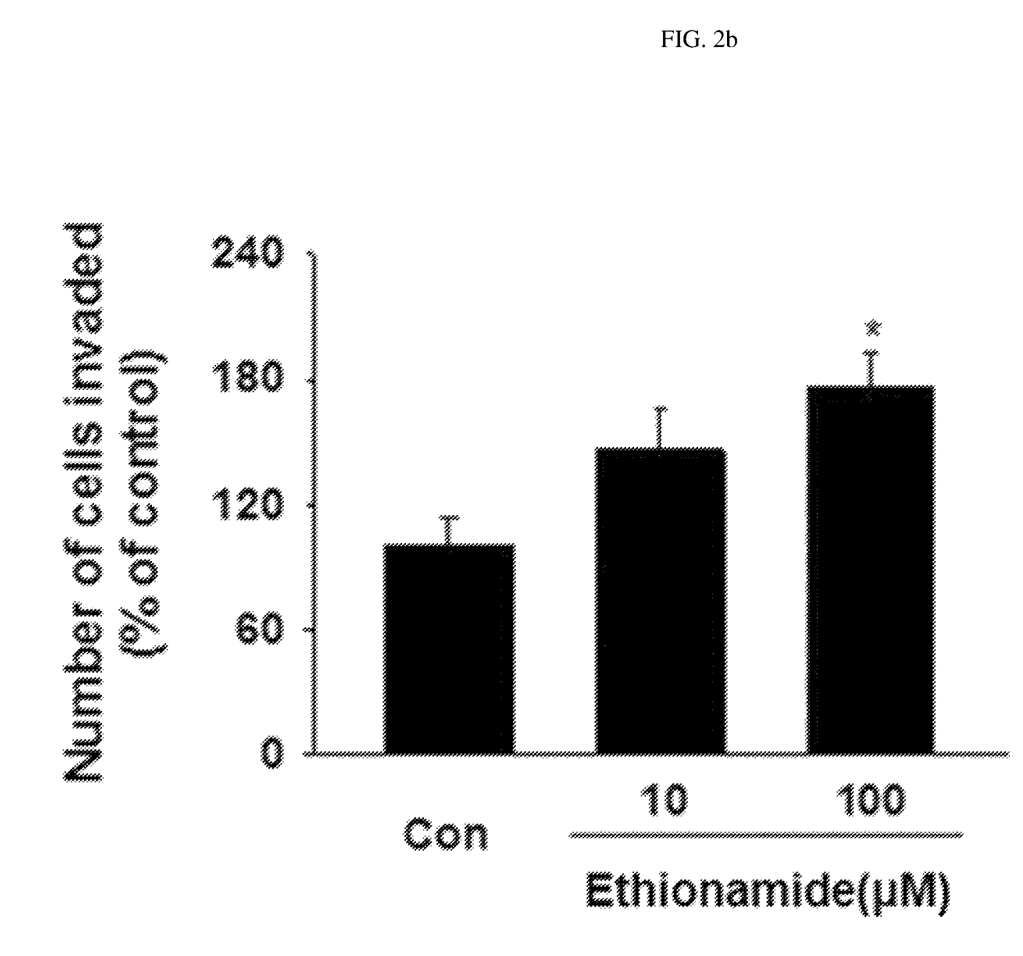
FIG. 2B is a quantitative result of measuring the number of migrating cells after a Transwell assay.

As a result, as shown in FIG. 2A, compared to a control not treated with ethionamide, in the ethionamide-treated groups (10 μM of ethionamide and 100 μM of ethionamide), the number of the stained stem cells increased, indicating that the invasion ability of the stem cells is increased by ethionamide treatment, and proportional to a concentration of the treated ethionamide. In addition, as shown in FIG. 2B, it was quantitatively confirmed that the invasion ability of human mesenchymal stem cells is significantly increased by ethionamide treatment.

Example 4

Verification of Expression Level of Gene Related to Migration of Human Mesenchymal Stem Cells by Ethionamide Treatment Based on the results of Examples 2 and 3, whether an expression level of a gene related to migration of stem cells is changed by ethionamide treatment was examined. To this end, the human mesenchymal stem cells prepared according to the method described in Example 1 were treated with ethionamide for 72 hours, and then lysed with TRIzol (Ambion, USA). Subsequently, following the addition of chloroform (Sigma Aldrich, USA) and centrifugation, only a supernatant was transferred to a new tube, treated with isopropanol (Amresco, USA), and centrifuged to precipitate RNA. Afterward, the precipitated RNA was treated with 75% ethanol (Merck Millipore, USA) for washing, and the completely dried RNA was dissolved in DEPC water (Biosesang, Korea). 5 μg of RNA extracted from the human mesenchymal stem cells treated or not treated with ethionamide by the above-described method was used for cDNA synthesis, and here, for the cDNA synthesis, a cDNA synthesis kit (Invitrogen, USA) was used. Afterward, 10 pM of a primer (Bioneer, Korea) specific for CXCR4, which is a gene related to stem cell migration, and a SYBR green master mix (Applied Biosystems, USA) were added to the synthesized cDNA, and cDNA was amplified using a real time-PCR device (Applied Biosystems, USA), followed by assessment of the amplified result to measure an initial amount of cDNA.

Figure 3:
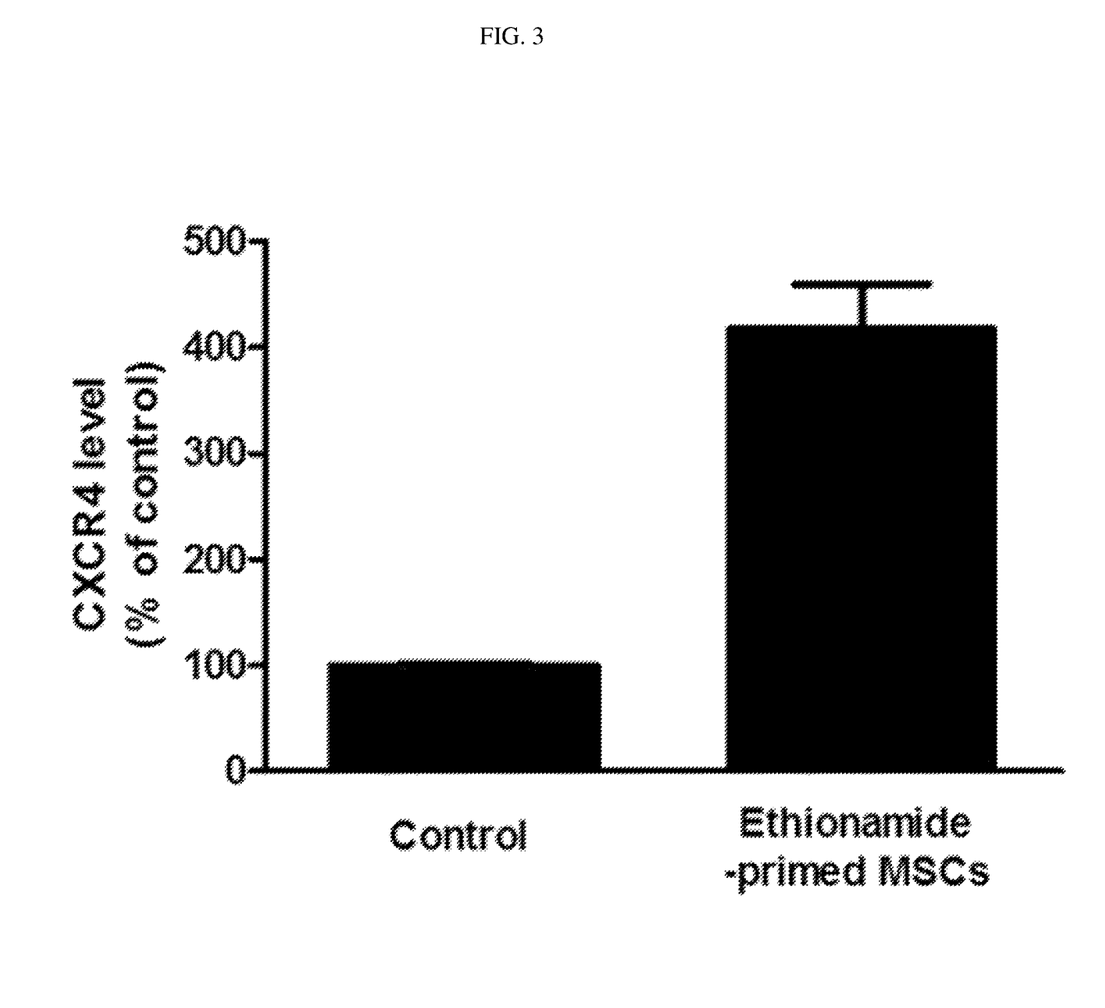
FIG. 3 is a result of measuring an expression level of CXCR4, which is a migration ability-related gene, in human mesenchymal stem cells which are treated or not treated with ethionamide through real-time polymerase chain reaction (real-time PCR).

As a result, as shown in FIG. 3, it was confirmed that, compared with the stem cells not treated with ethionamide (Control), in the ethionamide-treated stem cells (ethionamide-primed MSCs), the expression level of the CXCR4 gene was increased at least 4-fold.

It should be understood by those of ordinary skill in the art that the above description of the present invention is exemplary, and the exemplary embodiments disclosed herein can be easily modified into other specific forms without departing from the technical spirit or essential features of the present invention. Therefore, the exemplary embodiments described above should be interpreted as illustrative and not limited in any aspect.

INDUSTRIAL APPLICABILITY

The ethionamide according to the present invention retains the properties of human mesenchymal stem cells and significantly improves cell migration, and in the stem cell therapy field, the ethionamide and a medium composition containing the same promote the migration of stem cells to a damaged part, thereby increasing a therapeutic effect, and thus are expected to be effectively used in related fields.

The invention claimed is:

1. A method for producing a mesenchymal stem cell having increased chemokine (C-X-C motif) receptor 4 (CXCR4) gene expression as compared to a mesenchymal stem cell cultured in a medium not comprising ethionamide, the method comprising:
culturing mesenchymal stem cells in a medium comprising ethionamide for 72 hours, wherein the medium increases the expression of the CXCR4 gene in a mesenchymal stem cell compared to a mesenchymal stem cell cultured in the medium not comprising ethionamide, and wherein the ethionamide is contained in the medium at 100 µM.

2. The method of claim 1, wherein the medium is Minimum Essential Medium Alpha supplemented with fetus bovine serum (FBS) and gentamicin.

3. The method of claim 1, wherein the mesenchymal stem cells are derived from one or more types of tissue selected from the group consisting of the umbilical cord, umbilical cord blood, bone marrow, fat, muscle, nerve, skin, amniotic membrane and placenta.

4. A method of increasing chemokine (C-X-C motif) receptor 4 (CXCR4) gene expression in a mesenchymal stem cell as compared to a mesenchymal stem cell cultured in a medium not comprising ethionamide, the method comprising:

culturing mesenchymal stem cells in a medium comprising ethionamide for 72 hours, wherein the medium increases the expression of the CXCR4 gene in a mesenchymal stem cell compared to a mesenchymal stem cell cultured in the medium not comprising ethionamide, and wherein the ethionamide is contained in the medium at 100 µM.

5. The method of claim 4, wherein the mesenchymal stem cells are derived from one or more types of tissue selected from the group consisting of the umbilical cord, umbilical cord blood, bone marrow, fat, muscle, nerve, skin, amniotic membrane and placenta.

* * * * *